(12) United States Patent
Dasgupta et al.

(10) Patent No.: US 10,653,585 B2
(45) Date of Patent: May 19, 2020

(54) PALLADIUM BASED ALLOYS (71) Applicant: Ivoclar Vivadent AG, Schaan (LI)

(72) Inventors: Tridib Dasgupta, East Amherst, NY (US); George Tysowsky, East Amherst, NY (US)

(73) Assignee: Ivoclar Vivadent, Inc., Amherst, NY (US)

( * ) Notice: Subject to any disclaimer, the term of this patent is extended or adjusted under 35 U.S.C. 154(b) by 0 days.

(21) Appl. No.: 16/136,887

(22) Filed: Sep. 20, 2018

(65) Prior Publication Data

US 2019/0015300 A1 Jan. 17, 2019

Related U.S. Application Data (63) Continuation-in-part of application No. 14/381,145, filed as application No. PCT/US2013/029766 on Mar. 8, 2013, now Pat. No. 10,123,858.

(60) Provisional application No. 61/608,924, filed on Mar. 9, 2012.

(51) Int. Cl.
| | | |
|---|---|---|
| *A61C 8/00* | (2006.01) | |
| *A61K 6/04* | (2006.01) | |
| *A61K 6/02* | (2006.01) | |
| *C22C 5/04* | (2006.01) | |
| *B32B 15/04* | (2006.01) | |

(52) U.S. Cl.
CPC ............ *A61K 6/043* (2013.01); *A61K 6/0205* (2013.01); *B32B 15/04* (2013.01); *C22C 5/04* (2013.01); *B32B 2535/00* (2013.01)

(58) Field of Classification Search
CPC ........... A61C 5/70; A61C 5/73; A61C 8/0015; A61C 13/081; A61K 6/0017; A61K 6/0273; A61K 6/04; A61K 6/046; C22C 5/04; Y10T 428/24942
See application file for complete search history.

(56) References Cited

U.S. PATENT DOCUMENTS

| | | | |
|---|---|---|---|
| 3,819,366 A * | 6/1974 | Katz | ...................... A61K 6/046 420/463 |
| 4,681,735 A | 7/1987 | Groll et al. | |
| 4,877,402 A | 10/1989 | Hirabayashi et al. | |
| 5,290,371 A * | 3/1994 | Cameron | ............... A61K 6/046 148/442 |
| 5,298,218 A | 3/1994 | Groll et al. | |
| 6,200,137 B1 | 3/2001 | Holand et al. | |
| 6,290,501 B1 * | 9/2001 | Grau | .................... A61K 6/0205 420/463 |
| 2001/0012491 A1 | 8/2001 | Strietzel | |
| 2002/0041820 A1 | 4/2002 | Prasad | |
| 2006/0105297 A1 | 5/2006 | Knapp et al. | |
| 2008/0070058 A1 | 3/2008 | Dasgupta et al. | |
| 2011/0275033 A1 | 11/2011 | Dasgupta et al. | |

(Continued)

FOREIGN PATENT DOCUMENTS

| | | |
|---|---|---|
| EP | 0289097 A1 | 11/1988 |
| WO | 2009/120752 WO | 10/2009 |

*Primary Examiner* — Nicholas D Lucchesi
(74) *Attorney, Agent, or Firm* — Ann M. Knab; Thad McMurray (57) ABSTRACT

A palladium-based alloy having a coefficient of thermal expansion (CTE) of about 12.0 to about 13.0 and having one or more of the following additive metals: platinum, gallium, chromium, molybdenum, tin, silicon, ruthenium, rhenium, indium, tungsten, niobium, boron and lithium.

24 Claims, 2 Drawing Sheets (56) References Cited

U.S. PATENT DOCUMENTS

2012/0244035 A1* 9/2012 Cascone ............... C22C 30/00
                                                            420/583
2014/0170598 A1   6/2014 Abend

* cited by examiner

PALLADIUM BASED ALLOYS

CROSS-REFERENCE TO RELATED APPLICATIONS

This application claims priority and is a continuation-in-part of U.S. application Ser. No. 14/381,145, filed on Aug. 26, 2014, which is the National Stage application of International patent application PCT/US2013/029766 filed on Mar. 8, 2013, which claims priority to provisional application Ser. No. 61/608,924 filed Mar. 9, 2012, all of which are hereby incorporated by reference in their entirety.

FIELD OF THE INVENTION

This invention provides a novel palladium based alloy. The alloy can be used, for example, in making cast metal dental articles or restorations and, in particular, for press on metal (PoM) restorations.

BACKGROUND OF THE INVENTION

Since the late 1950s, dental crowns, bridges, and the like have been made with a composite including a cast metal substrate with a veneer of porcelain fabricated in such a manner that there is a bond between metal and porcelain such that the composite is stronger than the individual component parts. There are several aspects to be addressed when formulating such composites.

Aesthetics is one aspect to be considered. The primary reason for the use of such a composite is to reproduce the normal coloration of natural dentition. The enamel layer of healthy natural dentition is quite translucent and porcelain can be made with equal translucency. The translucency of enamel allows the color of healthy dentine to be seen. The dentine color normally has a yellowish tint. For a porcelain/alloy combination to be effective as a composite, a layer of oxide must be present on the alloy to form a bond with the porcelain. While high gold alloys may provide a suitable yellowish background for the porcelain for proper aesthetics, the alloying elements can form a dark gray to black colored oxide layer, which can screen out this underlying yellowish background color. Moreover, larger amounts of alloying elements form a colored oxide layer that can further reduce or eliminate the underlying gold color of the alloy.

Mechanical properties are another aspect to be considered. The American National Standards Institute/American Dental Association ("ANSI/ADA") specification #38 and International Organization for Standardization ("ISO") standard ISO9693 require a yield strength of at least 250 megapascal ("MPa") for the alloy. To attain such strength in gold-based alloys, significant amounts of alloying elements must be added, the result being alloys having a color that is closer to gray. It was thought that it is necessary to provide great strength because the alloy supported porcelain, which had little strength, particularly in tension, and zero ductility. Any slight deformation of the metal can cause fracture of the porcelain layer. The minimum for the standards mentioned above were set on the basis of testing alloys that were being successfully used at the time of the development of the standards. Subsequently, the minimum requirement has been questioned since alloys with less than this minimum have been used successfully. Also, it has been shown that the minimum requirement for single crowns should be lower than that for crowns composed of three or more unit bridges.

An unpublished work at the University of Kiel in Germany has indicated that from 30 to 35 kilograms of force causes pain to patients while, in one instance, 75 kilograms of force caused fracture of the tooth.

Physical properties are another aspect to be considered. Although the abovementioned standards do not require either minimum or maximum values for the coefficient of thermal expansion ("CTE"), these standards require that the CTE value be given for both porcelain and alloy. This is because the popular conception is that the coefficients of porcelain and metal should be "matched" in order to assure compatibility of the two. This concept fails to take into consideration that stresses between the two occur during cooling rather than during heating, and the cooling rates of porcelain and metal vary very significantly.

It is readily understood that the solidus of the alloy must be sufficiently higher than the firing temperature of the porcelain so that the alloy is not even partially melted during firing of the ceramic.

Chemical properties are another aspect to be considered. The bonding of porcelain to metal does not occur directly; rather it occurs between porcelain and a metal oxide layer. Normal PFM procedure is to heat the cast alloy to a suitable temperature to produce a metal oxide layer on the surface of the alloy. If this oxide does not adhere to the alloy, it can be simply removed by its attachment to the porcelain. Some of the bond is simply mechanical but the primary bonding takes place as a mutual solution of metal oxide in porcelain and vice versa known as diffusion bonding. If the oxide is not soluble in the porcelain and/or vice versa, no bonding takes place. When the porcelain is fired, small particles and larger particle surfaces are fused (melted) and this liquid porcelain and the metal oxide layer form a solution by either liquid or solid diffusion.

Although porcelain fused to metal restorations have been successful in the dental field, it would be advantageous to improve the wear resistance and flexural modulus of these restorations. Lithium silicate ceramics, including but not limited to lithium metasilicate and lithium disilicate, and similar strong ceramics have proven beneficial in the dental industry providing strong, resilient, aesthetically pleasing dental restorations. U.S. Pat. Nos. 6,455,451, 6,818,573, 6,802,894, 6,420,288, 6,342,458, 7,279,238, 7,316,740, 7,816,291, and 7,452,836 are directed to lithium silicate dental materials and are hereby incorporated by reference in their entirety.

In general, it is desirable that all alloys for dental applications are nonmagnetic. It was found that certain dental alloys create a magnetic effect that is not desirable in dental applications. It would be beneficial to provide a dental alloy with good corrosion resistance and having non-magnetic properties. Moreover, it would be advantageous to provide an alloy that is compatible with ceramics which have lower coefficients of expansion than leucite based feldspathic porcelains with a CTE range $12.6-14.0 \times 10^{-6}/°$ C. at 25-500° C.

The inventors herein have found that alloys having an excess of platinum or too much grain refiner may cause formation of a dendritic grain structure in the alloy matrix and/or segregation in the alloy matrix. This in turn can cause uneven strength in the structure or interfere with certain mechanical properties. It would be beneficial to reduce the amount of platinum and/or grain refiners in dental alloys to prevent formation of a dendritic grain structure and/or segregation in the alloy matrix.

SUMMARY

The present invention provides compositions, materials and techniques that can optionally address one or more of the abovementioned shortcomings associated with conventional technology.

An aspect of the present invention provides an alloy which can be manufactured by the normal melt process, cast into a bar and rolled to the required thickness or alternatively, by the atomization and compression method of U.S. Pat. No. 5,799,386 to Ingersoll et al. entitled Process Of Making Metal Castings, issued Sep. 1, 1998, which is incorporated herein by reference in its entirety.

Another aspect of the present invention provides an alloy which has a solidus high enough that no fusion occurs during firing of ceramics.

Another aspect of the present invention provides an alloy which has a CTE in a range that has been shown to be compatible with ceramics and glass ceramics.

Another aspect of the present invention is to provide an alloy which can be readily cast by normal dental procedures, and can be recast using normal dental laboratory procedures.

Another aspect of the present invention provides a cast alloy unit which can be ground and polished to a high shine.

Another aspect of the present invention provides an alloy which has a light oxide color that does not affect the apparent color of the ceramic or glass ceramic and the oxide does not increase during the firing of the ceramic or glass ceramic.

Another aspect of the present invention provides an alloy which when heated to the ceramic or glass ceramic firing temperature, a thin, continuous, tenacious oxide is formed and creates a strong bond between the alloy and the ceramic by diffusion bonding.

Another aspect of the present invention provides an alloy which has the strength to withstand loads in excess of those that would cause pain to the patient.

Another aspect of the invention provides a Pd based alloy with a low coefficient of thermal expansion.

Another aspect of the invention provides an alloy that can be cast into single unit, 3-unit, 4-unit and long span bridges.

Another aspect of the invention provides an alloy that is compatible with lithium silicate ceramics.

According to yet another aspect, an embodiment of the present invention provides a palladium platinum alloy that may include molybdenum and gallium.

According to a further aspect, the alloy exhibits non-magnetic properties and good corrosion resistance.

An alloy formed according to one embodiment of the invention is a palladium based alloy wherein palladium is about 74 to about 88 wt. %, platinum is about 3 to about 12 wt. %, gallium is about 1 to about 9 wt. %, molybdenum is up to about 5 wt. % and including minor amounts of ruthenium and rhenium. The coefficient of thermal expansion (CTE) is about 11.5 to about 13 (25-500° C.) and preferably about 12 to about 12.5 (25-500° C.) and 12.4 to about 13.8 (25-600° C.). From 0 wt. % up to about 15 wt. % of the following metals can be added to the base Pd alloy: tin, silicon, indium, niobium, tungsten, boron, lithium, tantalum, gold or combinations thereof.

An alloy formed according to another embodiment of the invention is a palladium based alloy having palladium, platinum, chromium, gallium, molybdenum, and one or more of ruthenium, rhenium, tin, silicon, indium, niobium, tungsten, boron, lithium, tantalum, and combinations thereof. The coefficient of thermal expansion (CTE) is about 11.5 to about 13 (25-500° C.) and preferably about 12 to about 13 (25-500° C.), more preferably, 12 to about 12.8, (25-500° C.), and 12.4 to about 13.8 (25-600° C.).

It is preferable that the alloy has the following components in the following amounts: palladium is about 74 to about 88 wt. %, platinum is up to about 8 wt. %, gallium is about 1 to about 9 wt. %, molybdenum is up to about 5 wt. % and including minor amounts of ruthenium and rhenium. From 0 wt. % up to about 15 wt. % of the following metals can be added to the base Pd alloy: chromium, tin, silicon, indium, niobium, tungsten, boron, lithium, tantalum, or combinations thereof, although it is preferably that chromium be present in at least 0.1%.

It is preferable that the alloy has a reduced amount of Pt and an added amount of one or more of Cr, Mo, Nb, alone or in combination in order to obtain the preferred CTE and also to prevent dendritic grain formation.

According to an additional aspect, the present invention provides one or more of the above-described alloys in combination with a ceramic or a glass ceramic material, which can optionally comprise porcelain.

According to further aspects, the alloy(s) and ceramic or glass ceramic are bonded together, optionally by an oxide layer. According to still further aspects, a dental article, such as, for example, a restoration such as a crown or a bridge can comprise the alloy and/or combination of the present invention. According to additional aspects, the ceramic or glass ceramic may be pressed onto the alloy substrate to form a dental restoration.

According to another aspect, it is preferably that the alloy is free of gold, copper, silver, and cobalt.

According to a further aspect, a dental restoration is provided having a dental alloy substrate free of gold, copper, silver and cobalt comprising palladium, platinum, gallium, molybdenum, ruthenium and/or rhenium and having a CTE in the range of about 12 to about $13.0 \times 10^{-6}$/° C. (25-500° C.), and a ceramic or glass ceramic having a CTE in the range of about 8.0 to about $13 \times 10^{-6}$/° C. (25-500° C.), pressed onto the dental alloy substrate.

According to a further aspect, an opaque may be applied onto the alloy before the ceramic or glass ceramic is pressed onto the alloy. It is preferable that the opaque has a CTE in the range of about 8 to about $13 \times 10^{-6}$/° C. (25-500° C.), or more preferably about 9.5 to about $12.5 \times 10^{-6}$/° C. (25-500° C.), or 9.0 to about $11.8 \times 10^{-6}$/° C. (25-500° C.) or 10.0 to about $11.5 \times 10^{-6}$/° C. (25-500° C.). The thickness of the opaque is typically no greater than 0.3 mm, preferably no greater than 0.2 mm and more preferably 0.05 to 0.1 mm.

These and other aspects of the present invention will become apparent upon a review of the following detailed description and accompanying examples which are recited herein as illustrative of the present invention but in no way limit the present invention.

BRIEF DESCRIPTION OF THE DRAWINGS

Further advantage, details and characteristics will arise from the following description of several illustrated embodiments of the invention by way of the drawings, wherein.

DETAILED DESCRIPTION

The alloys are based on a portion of the palladium-platinum binary system and have a coefficient of thermal expansion (CTE) in the range of about of about 11.5 to about 13.0 at 25°-500° C. or $12.0-12.7 \times 10^{-6}$/° C. at 25°-500° C., 12.0-13×10⁻⁶/° C. at 25°-500° C. and 12.4-13.0×10⁻⁶/° C. at 25°-600° C. The alloy of the invention can have a solidus high enough that no melting occurs during firing of glass ceramics and ceramics, and a coefficient (CTE) in a range that has been demonstrated to be compatible with glass ceramics and ceramics. It may include one or more of the following additive metals: Cr, Ga, Sn, Si, Ru, Re, In, Nb, Mo, Ta, W, B, and Li for dental prostheses to improve physical, chemical, mechanical and handling properties.

It may be used for the application of glass ceramics and ceramics having CTEs that are close to/compatible with the CTE of the alloy. Examples of suitable glass ceramics are lithium silicate ceramics including but not limited to, lithium metasilicate and lithium disilicate based glass ceramics. Other ceramics and glass ceramics having similar CTEs are also suitable for use with this alloy. Ceramics and glass ceramics having CTEs in the range of about 8 to about $13 \times 10^{-6}/°$ C. (25-500° C.), 8 to about $12.5 \times 10^{-6}/°$ C. (25-500° C.) and more preferably about 9 to about $12 \times 10^{-6}/°$ C. (25-500° C.), about 8 to about $11 \times 10^{-6}/°$ C. (25-500° C.), about 10 to about $11 \times 10^{-6}/°$ C. (25-500° C.), or about 12 to about $12.8 \times 10^{-6}/°$ C. (25-500° C.) also may be used with the alloys described herein.

The glass ceramic or ceramic with a low CTE may be pressed onto the metal substrate. The coefficient of thermal expansion for lithium silicates is about $10.55 \pm 0.35 \times 10^{-6}/°$ C. (100-500° C.). Any type of dental restoration may be fabricated including, but not limited to, single unit, short span and long span bridges.

The alloy and ceramics/glass-ceramics used herein require a certain opaque that will not induce cracking. The opaque should have a CTE which is between the CTE of the alloy onto which it is applied and the ceramic or glass-ceramic which is applied onto the opaque.

An opaque having a CTE in the range of about 9 to about $13 \times 10^{-6}/°$ C. (25-500° C.), more preferably about 10 to about $12 \times 10^{-6}/°$ C. (25-500° C.), or 10.5 to about $11.5 \times 10^{-6}/°$ C. (25-500° C.) may be applied onto the alloy before the ceramic or glass ceramic is applied. The thickness of the opaque is typically no greater than 0.3 mm, preferably no greater than 0.2 mm and more preferably 0.05 to 0.1 mm. The opaque is used as a bond layer between the alloy and the ceramic or glass-ceramic and also hides the color of the alloy so that it does not show through the ceramic or glass-ceramic.

There are several properties exhibited by alloy(s) of the present invention that make it suitable for press on metal (PoM) applications. The alloy is grey in color with an oxide coating for bonding glass ceramic or ceramic to the oxidized cast alloy substrate. The alloy has mechanical properties for cast prostheses and for the support of the glass ceramic or ceramic and is readily polished to a bright sheen.

The alloy of the invention can be readily cast by normal dental procedures, and can be recast using normal dental laboratory procedures. The cast alloy unit can be ground and polished to a high shine. The alloy can have a light oxide color that does not affect the apparent color of the ceramic or glass ceramic layer and the oxide does not increase during the firing of the ceramic or glass ceramic. When heated to the ceramic or glass ceramic firing temperature, a thin, continuous, and tenacious oxide is formed, which enters into a bond with the ceramic or glass ceramic. The alloy has a strength that withstands loads in excess of those that would cause pain to the patient.

The alloy of the present invention can meet aesthetic needs while using a palladium-platinum base. That is, the alloy system reproduces the normal coloration of natural dentition. The enamel layer of healthy natural dentition is quite translucent and ceramic or glass ceramic can be made with similar translucency. The translucency of enamel allows the color of healthy dentine to be seen. This color normally has a yellowish tint. With the ceramic or glass ceramic alloy combination, a layer of oxide must be present to form a bond with the ceramic or glass ceramic. While high gold alloys may provide a yellowish background for the ceramic or glass ceramic, other metals such as palladium, platinum etc., provide a suitable gray background.

Moreover, applying or pressing a high strength ceramic or glass ceramic such as lithium silicate onto the metal framework provides not only good aesthetic properties but also excellent wear resistance reducing brittleness and chipping that may result when using porcelain-fused-to metal (PFM) restorations.

It has been found that reducing the amount of platinum and replacing with elements such as chromium, molybdenum, and/or niobium while maintaining a certain amount of grain refiners reduces the formation of a dendritic grain structure and/or segregation in the alloy matrix, which can cause uneven strength in the structure or interfere with certain mechanical properties. Formation of a dendritic grain structure can occur from an excess of platinum. The chromium, molybdenum, and/or niobium can also reduce the CTE.

For proper bonding, the alloying elements form an oxide on the cast metal surface. This dark gray to black colored oxide layer, can affect the apparent color of the ceramic or glass ceramic veneering layer. The alloy system of the present invention may include elements added to regulate the amount and color of the oxide layer and melting characteristics, selected from the group including, but not limited to: indium, tin, boron, silicon, and/or gallium.

The mechanical properties of the alloy follow ANSI/ADA specification #38 and ISO standard ISO22674 and IS09693 which require a 0.2% offset proof stress/yield stress or yield strength of at least about 250 MPa for the alloy. This alloy exhibits much higher yield strength of greater than about 360 MPa with % elongation greater than about 5.0 to qualify as a Type 4 alloy per ISO 22674. To attain such strength, significant amounts of alloying elements such as, but not limited to, platinum. gallium, indium, tin, silicon, molybdenum and/or tungsten may be added to the alloy formulation.

The above mentioned standards do not require minimum or maximum values for coefficient of thermal expansion (CTE); however, physical properties including the CTE value for both ceramic or glass ceramic and alloy may be regulated. The alloy of the invention may include elements added to regulate the grain size, selected from the group including, but not limited to: gallium, tungsten, rhenium and/or ruthenium. Elements that can be added to regulate oxidation during melting and casting include but are not limited to: boron, lithium, silicon, and/or gallium. Also, heat transfer rate may be taken into consideration. When cooling from the ceramic or glass ceramic firing temperature, shrinkage of both ceramic or glass ceramic and alloy take place and the alloy, which cools faster, shrinks faster and thus puts tensile forces on the ceramic or glass ceramic to metal bond. If this disparity of shrinkage is too much, the ceramic or glass ceramic will no longer be bonded to the alloy or the ceramic or glass ceramic will crack when the composite reaches room temperature. An alloy that is compatible with ceramics or glass ceramics will have a CTE that is in a range that is closely matched to the CTE range of the ceramic or glass ceramic that will be fused to the alloy. Closely matching the CTE of an alloy to the CTE of a ceramic or glass ceramic will diminish the likelihood that the ceramic will debond from the alloy after fusing, or that cracks will develop in the ceramic or glass ceramic after fusing to the alloy. Examples provided herein offer alloys that have been developed that have CTE values that are matched appropriately.

It is readily understood that the solidus of the alloy must be sufficiently higher than the firing temperature of the ceramic or glass ceramic so that the alloy is not even partially melted during firing. Concerning the bonding of the ceramic or glass ceramic to the alloy of the invention, it does not occur between ceramic or glass ceramic and metal, it occurs between ceramic or glass ceramic and the metal oxide layer formed when the alloy is heated prior to and during the firing of the ceramic or glass ceramic. If the oxide is not adherent to the alloy, it can be simply removed by the ceramic or glass ceramic. Some of the bond is simply mechanical but the primary bonding takes place as diffusion of metal oxide in ceramic or glass ceramic and vice versa. If the oxides are not soluble in the ceramic or glass ceramic and/or vice versa, no bond takes place. When the ceramic or glass-ceramic is fired, small particles and larger particle surfaces are fused (melted) and this liquid glass ceramic and the metal oxide layer form a solution by either liquid or solid diffusion. This concept is further described in copending U.S. application Ser. Nos. 11/892,933 and 13/181,172, which are hereby incorporated by reference.

For certain alloys herein, the solidus point, which is defined by the starting of the melting range, is at least about 950° C. and preferably greater than about 1050° C. in order to accommodate the use of high fusing ceramic or glass ceramics in the market without any distortion of the dental prosthesis. It further allows repair work using pre-solders available in the market with no damage to the restoration. For certain alloys herein, the liquidus point, which is defined by the end of the melting range is not greater than about 1380° C. for easy melting of the alloy. For most of the induction casting machines on the market, the maximum temperature limit is 1500° C. In order to melt the metal and reach the proper fluidity for casting, at least 100° C. above the liquidus point of the alloy must be reached.

It is preferable that the composition comprises the following components in Table 1 or Table 2:

TABLE 1

| Element | Weight Percent Range 1 | Weight Percent Range 2 | Weight Percent Range 3 | Weight Percent Range 4 |
|---|---|---|---|---|
| Palladium | about 74.5%-about 88.5% | about 76.0%-about 86.0% | about 79.5%-about 85.0% | about 79%-about 85% |
| Platinum | about 3.6%-about 12.0% | about 4%-about 10.0% | about 5.0%-about 9.0% | about 5.5%-about 7.0% |
| Gallium | about 1.7%-about 9% | about 2.5%-about 8.5% | about 4.2%-about 8.5% | about 5.0%-about 8% |
| Molybdenum | about 0.1%-about 5.0% | about 0.1%-about 4.5% | about 0.1%-about 4.0% | about 0.5%-about 3.6% |
| Tin | 0-about 7.0% | about 0.5%-about 6.0% | about 0.5%-about 5.0% | about 0.5%-about 3.5% |
| Silicon | 0-about 1.2% | 0-about 1.2% | 0-about 1.2% | 0-about 1.2% |
| Ruthenium | about 0.1%-about 0.8% | about 0.1%-about 0.8% | about 0.1%-about 0.8% | about 0.1%-about 0.8% |
| Rhenium | about 0.1%-about 0.8% | about 0.1%-about 0.8% | about 0.1%-about 0.8% | about 0.1%-about 0.8% |
| Indium | 0-about 7.0% | about 0.5%-about 6.0% | about 0.5%-about 5.0% | about 0.5%-about 3.5% |
| Niobium | 0-about 1.0% | 0-about 1.0% | 0-about 1.0% | 0-about 1.0% |
| Tungsten | 0-about 0.5% | 0-about 0.5% | 0-about 0.5% | 0-about 0.5% |
| Boron | 0-about 0.1% | 0-about 0.1% | 0-about 0.1% | 0-about 0.1% |
| Lithium | 0-about 0.10% | 0-about 0.1% | 0-about 0.1% | 0-about 0.1% |
| Tantalum | 0-about 1.0% | 0-about 0.4% | 0-about 0.3% | 0.5-about 0.2% |
| Gold | 0-about 8% | about 0.6-about 6.0% | about 0.6-about 5.0% | 0-about 1.6 |

TABLE 2

| Element | Weight Percent Range 1 | Weight Percent Range 2 | Weight Percent Range 3 | Weight Percent Range 4 |
|---|---|---|---|---|
| Palladium | about 74.5%-about 88.5% | about 76.0%-about 86.0% | about 79.5%-about 85.0% | about 79%-about 85% |
| Platinum | about 0.1%-about 8.0% | about 0.1%-about 6.0% | about 0.1%-about 5.0% | about 0.1%-about 4.0% |
| Gallium | about 1.7%-about 9% | about 2.5%-about 8.5% | about 3.5%-about 8.5% | about 4.0%-about 8% |
| Molybdenum | about 0.5%-about 5.0% | about 0.1%-about 4.5% | about 0.1%-about 4.0% | about 0.5%-about 3.6% |
| Tin | 0-about 7.0% | about 0.5%-about 6.0% | about 0.5%-about 5.0% | about 0.5%-about 3.5% |
| Silicon | 0-about 1.2% | 0-about 1.2% | 0-about 1.2% | 0-about 1.2% |
| Ruthenium | about 0.1%-about 0.8% | about 0.1%-about 0.8% | about 0.1%-about 0.8% | about 0.1%-about 0.8% |

TABLE 2-continued

| Element | Weight Percent Range 1 | Weight Percent Range 2 | Weight Percent Range 3 | Weight Percent Range 4 |
|---|---|---|---|---|
| Rhenium | about 0.1%-about 0.8% | about 0.1%-about 0.8% | about 0.1%-about 0.8% | about 0.1%-about 0.8% |
| Indium | 0-about 7.0% | about 0.5-about 6.0% | about 0.5-about 5.0% | about 0.5-about 3.5% |
| Niobium | 0-about 1.5% | 0-about 1.0% | 0-about 1.0% | 0-about 1.0% |
| Tungsten | 0-about 4.0% | 0-about 3.0% | 0-about 2.0% | 0-about 2.0% |
| Boron | 0-about 0.1% | 0-about 0.1% | 0-about 0.1% | 0-about 0.1% |
| Lithium | 0-about 0.10% | 0-about 0.1% | 0-about 0.1% | 0-about 0.1% |
| Tantalum | 0-about 1.0% | 0-about 0.4% | 0-about 0.3% | 0.05-about 0.2% |
| Chromium | 0-about 6% | 0-about 5.0% | 0-about 4.5% | 0-about 4.5% |

The C.T.E (at 25-600° C.) of the alloys should be between about 12.0 and about 13.8×10$^{-6}$/° C. The CTE (at 25-500° C.) of the alloys should be between about 11.5 and about 13.0×10$^{-6}$/° C. and preferably between about 12.0 and about 13.0×10$^{-6}$/° C. more preferably between about 12.0 and about 12.8×10$^{-6}$/° C. in order to work with most of the high fusing ceramic or glass ceramics on the market. It is preferable that the CTE not exceed 13.0×10$^{-6}$/° C.

It should be noted that any incremental sub-ranges within the ranges specifically identified are also covered as useable alloys herein. Ranges of increments of 0.001% within those ranges are contemplated to be possible examples of the present invention.

The gallium, indium, tin, silicon and boron in the composition aid in controlling the liquidus temperature and improve the melting and casting properties. The platinum, niobium, molybdenum and tungsten in the composition assist in controlling the CTE, more specifically, in reducing the CTE.

The combination of In, Sn, Si, Ga, B, and Li reduces the temperature, improves the fluidity of the molten alloy and controls the CTE. The combination of Pt and Pd increases the corrosion resistance, controls the CTE and improves biocompatibility. The combination of Pt, Mo and W controls the CTE by reducing the number. It is preferable that the combination of Pt and Pd are equal to or greater than about 75%. It is preferable that the Pt is greater than about 10% to assist in lowering the CTE of the alloy.

Although the combination of Au having a melting temperature of 1065° C. and Pd having a melting temperature of 1554° C. provides an optimal melting temperature for the dental alloy, compatible with many dental ceramic or glass ceramics, it is preferable to have a gold-free, copper-free, cobalt-free and silver-free alloy in order to achieve a low CTE compatible with the low CTEs of the glass ceramics and ceramics such as lithium silicate ceramics.

Moreover, the compositions set forth in Tables are non-magnetic.

The following examples are for the purpose of illustration. It is understood that such detail is solely for that purpose, and variations can be made therein by those skilled in the art without departing from the spirit and scope of the invention which is defined by the following claims.

Examples 1-31

TABLE 3

| | Example No. | | | | | | | | |
|---|---|---|---|---|---|---|---|---|---|
| | 1 | 2 | 3 | 4 | 5 | 6 | 7 | 8 | 9 |
| Pd | 74.5 | 76 | 79.5 | 79.5 | 79.2 | 84.9 | 85.2 | 85.9 | 85.5 |
| Pt | 5 | 4.6 | 5 | 5 | 5 | 4.5 | 5.2 | 4.5 | 4.5 |
| Ga | 6.5 | 6 | 3.8 | 3.9 | 1.7 | 9 | 7.8 | 5.6 | 8.4 |
| Sn | 7 | 7 | 4.5 | 4 | 3.6 | 0.8 | 1.0 | 1.4 | 0.5 |
| Si | 0.8 | 0.8 | 1.2 | 1.2 | 0.5 | 0.1 | 0.1 | — | — |
| Ru | 0.1 | 0.1 | 0.1 | 0.1 | 0.1 | 0.6 | 0.6 | 0.5 | 0.8 |
| Re | 0.1 | 0.1 | 0.1 | 0.1 | 0.1 | 0.1 | 0.1 | 0.5 | 0.3 |
| In | — | — | — | — | 1.2 | — | — | — | — |
| Nb | — | — | — | — | 0.6 | — | — | — | — |
| Mo | — | — | — | — | — | — | — | — | — |
| B | — | — | — | — | — | — | — | — | — |
| Li | — | — | — | — | — | — | — | — | — |
| Au | 6 | 5 | 5.8 | 6.2 | 8 | — | — | 1.6 | — |
| Melting Range | 816.9-834 C. | 815.5-836 C. | 771-803 C. | 763-796 | 794-804 | 1076-1217 | 820-1112 C. | 810-1100 C. | 812-1113 C. |
| CTE (25-500 C.) | 12.55 | 12.6 | 12.62 | 12.43 | 12.24 | 12.97 | 13.1 | 12.66 | 13.2 |
| CTE (25-600 C.) | 12.96 | 13.01 | 12.83 | 12.7 | 12.52 | 13.25 | 13.3 | 13.0 | 13.4 |
| Hardness | | | | | | | HvAC: 278 HvPC$_{IL}$: 284 | HvAC: 181 HvPC$_{IL}$: 170 | HvAC: 250 HvPC$_{IL}$: 241 |

TABLE 4

| | Example No. | | | | | | | | |
|---|---|---|---|---|---|---|---|---|---|
| | 10 | 11 | 12 | 13 | 14 | 15 | 16 | 17 | 18 |
| Pd | 88.1 | 88.5 | 84.9 | 85 | 84 | 84 | 84 | 83 | 81.5 |
| Pt | 3.9 | 3.6 | 4.5 | 4.5 | 5.5 | 5.5 | 5.5 | 6 | 7 |
| Ga | 6.0 | 5.3 | 8 | 8.6 | 7.1 | 8.1 | 8.1 | 7.5 | 7.5 |
| Sn | 0.8 | 1.2 | 0.8 | 0.7 | 0.6 | 0.6 | — | 0.7 | 0.7 |
| Si | — | — | — | — | — | — | — | — | — |
| Ru | 0.8 | 0.8 | 0.6 | 0.6 | 0.6 | 0.8 | 0.8 | 0.6 | 0.6 |
| Re | 0.4 | 0.6 | 0.6 | 0.6 | 0.6 | 0.6 | 0.6 | 0.6 | 0.6 |
| In | — | — | — | — | — | — | 0.6 | — | — |
| Nb | — | — | — | — | 1.0 | — | — | 0.8 | 0.6 |
| Mo | — | — | — | — | — | 0.4 | 0.4 | 0.8 | 1.5 |
| B | — | — | — | — | — | — | — | — | — |
| Li | — | — | — | — | — | — | — | — | — |
| Au | — | — | 0.6 | — | 0.6 | — | — | — | — |
| Melting Range | 932.7-1095 C. | 971.4-1131 C. | 1204-1287 C. | 1180-1258 C. | 1004-1244 C. | 1206-1272 C. | 1194-1257 C.; 1201-1273 C. | 1168-1228 C.; 1197-1220 C. | 1189-1209 C. |
| CTE (25-500 C.) | 12.78 | — | 12.84 | 12.97 | 13.41-13.57 | 13.5 | 13.47 | 13.36 | 13.10-13.25 |
| CTE (25-600 C.) | 13.10 | — | 13.14 | 13.20 | 13.62-13.75 | 13.75 | 13.74 | 13.58 | 13.35-13.54 |
| Hardness | HvAC: 189 HvPC$_{IL}$: 187 | HvAC: 179 HvPC$_{IL}$: 177 | HvAC: 221 HvPC$_{IL}$: 188 | HvAC: 247 HvPC$_{IL}$: 237 | HvAC: 227 HvPC$_{IL}$: 240 | HvAC: 234 HvPC$_{IL}$: 231 | HvAC: 245 HvPC$_{IL}$: 246 | HvAC: 237 HvPC$_{IL}$: 242 | HvAC: 233 HvPC$_{IL}$: 235 |

TABLE 5

| | Example No. | | | | | | | |
|---|---|---|---|---|---|---|---|---|
| | 19 | 20 | 21 | 22 | 23 | 24 | 25 | 26 |
| Pd | 80.6 | 80 | 79.2 | 79.07 | 78.85 | 70.05 | 68.70 | 80.0 |
| Pt | 7.4 | 7.2 | 7.4 | 7.5 | 7.5 | 9.0 | 12.0 | 7.5 |
| Ga | 8 | 8 | 8 | 8 | 8 | 8.5 | 8.0 | 7.5 |
| Sn | 0.6 | 0.5 | 0.6 | 0.5 | 0.5 | — | — | 0.5 |
| Si | — | — | — | — | — | — | — | — |
| Ru | 0.5 | 0.4 | 0.4 | 0.4 | 0.4 | — | — | 0.5 |
| Re | 0.5 | 0.4 | 0.4 | 0.4 | 0.4 | 0.8 | 0.6 | 0.5 |
| In | — | — | — | — | — | 6.0 | 7.5 | — |
| Ta | — | — | — | — | — | — | — | 0.1 |
| Nb | 0.4 | 0.4 | 0.4 | 0.5 | 0.5 | — | — | — |
| Mo | 2 | 3.1 | 3.6 | 3.5 | 3.5 | 5.0 | 3.0 | — |
| W | — | — | — | — | — | 0.5 | — | — |
| B | — | — | — | 0.08 | 0.08 | 0.05 | 0.10 | — |
| Li | — | — | — | 0.05 | 0.10 | 0.10 | 0.10 | 0.1 |
| Au | — | — | — | — | — | — | — | — |
| Melting Range | 1100-1180 C. | 1101-1185 C.; 1092-1208 C. | 1087-1169 C.; 1109-1200 C. | 1083-1206 C.; 1080-1181 C. | 1100-1205 C. | 1040-1089 C. | 1039-1091 C. | 1131.9-1190 C. |
| CTE (25-500 C.) | 13.19 | 12.99 | 12.92-13.09 | 12.67; 12.46; 12.63 | 12.45 | 12.8 | 13.00 | 12.5 |
| CTE (25-600 C.) | 13.5 | 13.29 | 13.16-13.35 | 12.87; 12.79; 12.96 | 12.70 | 13.09 | 13.30 | — |
| Hardness | HvAC: 231 HvPC$_{IL}$: 231 | HvAC: 239 HvPC$_{IL}$: 212 | HvAC: 249 HvPC$_{IL}$: 223 | HvAC: 247; HvPC$_{IL}$: 245 | HvAC: 245 HvPC$_{IL}$: −240 | HvAC: 396; HvPC$_{IL}$: 389 | HvAC: 414; HvPC$_{IL}$: 398 | — |

TABLE 6

| | Example No. | | | | |
|---|---|---|---|---|---|
| | 27 | 28 | 29 | 30 | 31 |
| Pd | 84.6 | 82.55 | 83.6 | 83.9 | 83.4 |
| Pt | 6.1 | 0.10 | 1.2 | 3.0 | 8.0 |
| Ga | 3.0 | 3.3 | 5.0 | 5.0 | 5.0 |
| Sn | 1.2 | — | — | — | — |
| Cr | — | 4.0 | 4.0 | 3.2 | 1.6 |
| Si | — | — | — | — | — |
| Ru | 0.15 | 0.15 | 0.15 | 0.10 | 0.075 |
| Re | 0.15 | — | — | 0.10 | 0.075 |
| In | 1.2 | 2.3 | 1.0 | 0.40 | 0.40 |
| Ta | — | — | — | — | — |
| Nb | — | — | 1.0 | 0.40 | — |

TABLE 6-continued

| | Example No. | | | | |
|---|---|---|---|---|---|
| | 27 | 28 | 29 | 30 | 31 |
| Mo | 1.5 | 3.5 | 4.0 | 3.40 | 1.0 |
| W | 2.0 | — | — | 0.40 | 0.40 |
| B | 0.1 | 0.1 | — | — | — |
| Li | — | — | 0.05 | 0.10 | 0.05 |
| Au | — | — | — | — | — |
| Co | — | 4.0 | — | — | — |
| Melting Range | 1103-1333° C. | 830 C. Eutectic | 1224-1346° C. | 1136.5-1327.3° C. | 1188° C.-1312° C. |
| CTE (25-500 C.) | 12.49 | 13.25 | 12.69 | 12.73 | 12.83 |
| CTE (25-600 C.) | 12.70 | 13.44 | 12.95 | 12.95 | 13.03 |
| Hardness | HvAC: 151 | HvAC: 206 | | 192 Hv | 167 Hv |

Figure 1:
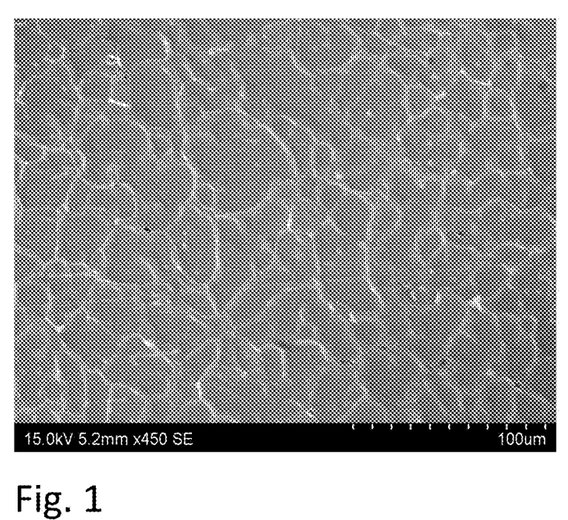
FIG. 1 shows an SEM image at 450× magnification of grain structure of a palladium base alloy.

FIG. 1 shows grain structure of the alloy from Example 27. The alloy contains 6.1% by wt Pt with grain refiners Ru and Re in an amount of each of Ru and Re of 0.15. The grain structure shows equi-axial grains.

Figure 2:
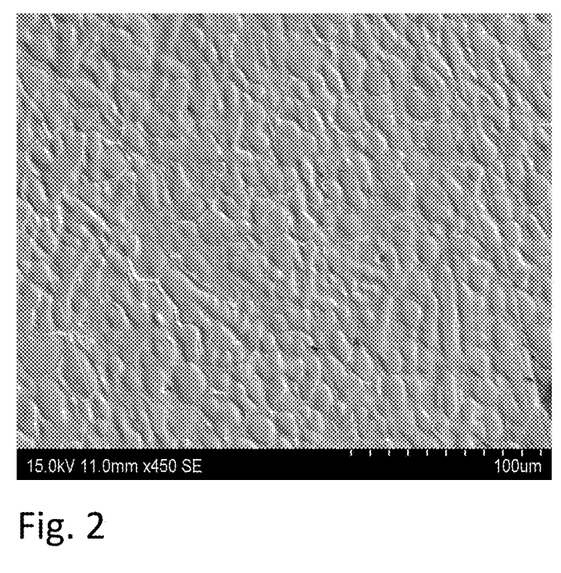
FIG. 2 shows an SEM image at 450× magnification of grain structure of a palladium base alloy.

FIG. 2 shows grain structure of the alloy from Example 29. The alloy contains 1.2% by wt Pt with grain refiner Ru in an amount of 0.15. Cr and Mo are present in an amount of 4.0% by wt. Nb is present in an amount of 1.0% by wt. The grain structure shows equi-axial grains.

Figure 3:
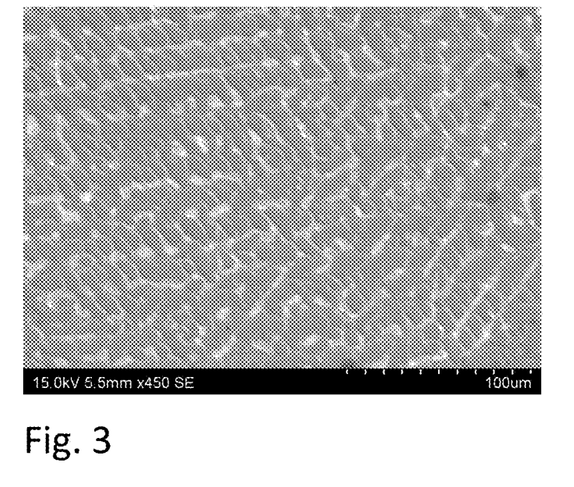
FIG. 3 shows an SEM image at 450× magnification of grain structure of a palladium base alloy.

FIG. 3 shows grain structure of the alloy from Example 30. The alloy contains 3.0% by wt Pt with grain refiners Ru and Re in an amount of each of Ru and Re of 0.10. Cr and Mo are present in an amount of 1.6 and 1.0% by wt, respectively. The grain structure shows some dendritic grains.

Figure 4:
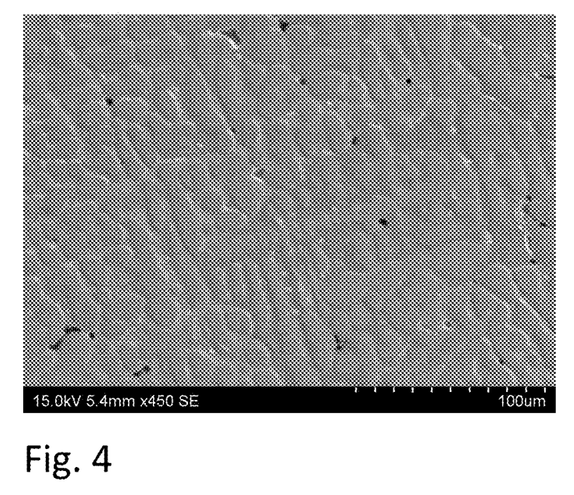
FIG. 4 shows an SEM image at 450× magnification of grain structure of a palladium base alloy.

FIG. 4 shows grain structure of the alloy from Example 31. The alloy contains 8.0% by wt Pt with grain refiners Ru and Re in an amount of each of Ru and Re of 0.075. Cr and Mo are present in an amount of 3.2 and 3.4% by wt, respectively. Nb is present in an amount of 0.4% by wt. The grain structure shows a very high amount of dendritic grains.

As represented in the photo micrographs by a scanning electron microscope (SEM), the grain structure is relative to the amount of Pt present in combination with the amount of grain refiners. If too much Pt is present with not enough grain refiners, dendritic grains form, which affect the mechanical properties of the final product. It is preferable to have an equi-axial grain structure in order to provide optimal mechanical properties in the final product. FIGS. 1 and 2 show preferable grain structure. FIG. 3 shows grain structure beginning to form dendrites, which structure could improve if higher amounts of grain refiners were added.

It is further preferable that the amount of Pt is not higher than 8.0 weight percent, the amount of one or more grain refiners is not less than 0.10 weight percent, and the amount of one or more of Cr, W, and Nb is at least 3.5 weight percent.

All numbers expressing quantities of ingredients, constituents, reaction conditions, and so forth used in the specification are to be understood as being modified in all instances by the term "about." Notwithstanding that the numerical ranges and parameters set forth, the broad scope of the subject matter presented herein are approximations, the numerical values set forth are indicated as precisely as possible. Any numerical value, however, may inherently contain certain errors resulting, for example, from their respective measurement techniques, as evidenced by standard deviations therefrom.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

We claim:

1. A dental article comprising;
   a dental alloy substrate free of gold, copper, silver and cobalt comprising palladium, platinum, gallium, molybdenum, chromium, ruthenium and rhenium and having a CTE in the range of about 11.5 to about $13.0 \times 10^{-6}/°$ C. at 25-500° C.; and
   a ceramic or glass ceramic having a CTE in the range of about 8.0 to about $13 \times 10^{-6}/°$ C. at 25-500° C. pressed onto the dental alloy substrate.

2. The dental article of claim 1, wherein the CTE of the dental alloy is in the range of about 12 to about $13.0 \times 10^{-6}/°$ C. at 25-500° C.

3. The dental article of claim 1, wherein the CTE of the ceramic or glass ceramic is in the range of about 9 to about $12.5 \times 10^{-6}/°$ C. at 25-500° C.

4. The dental article of claim 1, wherein the ceramic or glass ceramic comprises lithium silicate.

5. The dental article of claim 4, wherein the lithium silicate comprises lithium metasilicate, lithium disilicate or a mixture thereof.

6. The dental article of claim 1 fabricated as a crown, bridge, veneer, inlay, onlay, partial crown, fixed partial denture, implant abutment, implant, orthodontic appliance, space maintainer, tooth replacement appliance, splint, dentures, post, teeth, jacket, facing, veneer, facet, cylinder, or connector.

7. The dental article of claim 1, wherein the dental alloy substrate comprises a range of elements as follows:

| | |
|---|---|
| palladium | about 74.5 to about 88.5 |
| platinum | about 0.1 to about 8.0 |
| gallium | about 1.7 to about 9 |
| molybdenum | about 0.5 to about 5.0 |
| ruthenium | about 0.1 to about 0.8 |
| rhenium | about 0.1 to about 0.8 |
| chromium | about 0.1 to about 6.0. |

8. The dental article of claim 7 wherein the dental alloy substrate further comprises one or more of the following in weight percent:

| | |
|---|---|
| tin | 0 to about 7.0 |
| indium | 0 to about 7.0 |
| niobium | 0 to about 1.5 |

| | |
|---|---|
| tungsten | 0 to about 4.0 |
| boron | 0 to about 0.1 |
| lithium | 0 to about 0.1 |
| silicon | 0 to about 1.2 |
| tantalum | 0 to about 1 |

9. The dental article of claim 1, wherein the wherein the chromium is at least about 0.5 percent by weight of the total alloy.

10. The dental article of claim 1, wherein the platinum is no higher than 8% percent by weight of the total alloy.

11. The dental article of claim 1, wherein the chromium is at least about 0.1 percent by weight of the total alloy.

12. The dental article of claim 1, wherein the molybdenum is at least about 0.1 percent by weight of the total alloy.

13. The dental article of claim 1 further comprising an opaque layer between the dental alloy substrate and the ceramic or glass ceramic.

14. The dental article of claim 13 wherein the opaque layer has a CTE in the range of about 9.0 to about 13.0×$10^{-6}$/° C. at 25-500° C.

15. The dental article of claim 13 wherein the opaque layer has a CTE in the range of about 10.8 to about 12.0×$10^{-6}$/° C. at 25-500° C.

16. The dental article of claim 1 wherein the dental alloy is non-magnetic.

17. The dental article of claim 1 wherein the amount of Pt is not higher than 8.0 weight percent, an amount of one or more grain refiners is not less than 0.10 weight percent, and one or more of Cr, W, and Nb is at least 3.5 weight percent.

18. A dental alloy free of gold, copper, silver and cobalt comprising palladium, platinum, gallium, molybdenum, chromium, ruthenium and rhenium and having a CTE in the range of about 11.5 to about 13.0×$10^{-6}$/° C. at 25-500° C.

19. A dental alloy of claim 18 wherein the CTE is in the range of about 12 to about 13.0×$10^{-6}$/° C. at 25-500° C.

20. The dental alloy of claim 18 wherein the chromium is at least about 0.1 percent by weight of the total alloy.

21. The dental alloy of claim 18 wherein the platinum is no higher than 8% percent by weight of the total alloy.

22. The dental alloy of claim 18 having a solidus melting temperature in the range of about 980° C. to about 1250° C.

23. The dental alloy of claim 18 having a liquidus melting temperature in the range of about 1150° C. to about 1380° C.

24. A dental article comprising;
    a dental alloy substrate free of gold, copper, silver and cobalt comprising palladium, platinum, gallium, molybdenum, chromium, ruthenium and rhenium and having a CTE in the range of about 11.5 to about 13.0×$10^{-6}$/° C. at 25-500° C.;
    a ceramic or glass ceramic having a CTE in the range of about 9.0 to about 13×$10^{-6}$/° C. at 25-500° C. pressed onto the dental alloy substrate; and
    an opaque layer applied between the dental alloy substrate and the ceramic or glass ceramic having a CTE in the range of about 9.0 to about 13.0×$10^{-6}$/° C. at 25-500° C.

* * * * *